United States Patent [19]

Kim et al.

[11] Patent Number: 5,523,191
[45] Date of Patent: Jun. 4, 1996

[54] POSITIVE PHOTORESIST COMPOSITION CONTAINING NAPHTHOQUINONE DIAZIDE PHOSPHAZENE ESTERIFICATION PRODUCT

[75] Inventors: Seong-Ju Kim, Daejeon Yuseong; Ki-Dae Kim, Daejeon; Hosull Lee; Dae Y. Lee, both of Seoul, all of Rep. of Korea

[73] Assignee: Korea Kumho Chemical Co., Ltd., Seoul, Rep. of Korea

[21] Appl. No.: 379,190

[22] Filed: Jan. 27, 1995

[30] Foreign Application Priority Data

Oct. 27, 1994 [KR] Rep. of Korea .................. 1994-27707

[51] Int. Cl.$^6$ .................................................. G03F 7/023
[52] U.S. Cl. ............................ 430/192; 430/191; 430/193
[58] Field of Search ..................................... 430/191, 192, 430/193, 190; 534/557

[56] References Cited

PUBLICATIONS

Ahn et al., Journal of Photopolymer Science & Technology, vol. 5, No. 1, 1992, pp. 67–77.

Primary Examiner—Charles L. Bowers, Jr.
Assistant Examiner—Christopher G. Young
Attorney, Agent, or Firm—Harrison & Egbert

[57] ABSTRACT

There are disclosed novel photoresist compositions employing phosphazene compounds as ballast, unabsorbent of light at a band of i-line and g-line and superior in thermal resistance and sensitivity as well as resolution, characterized by introducing photosensitive groups into phosphazene type ballast represented by the following formula I:

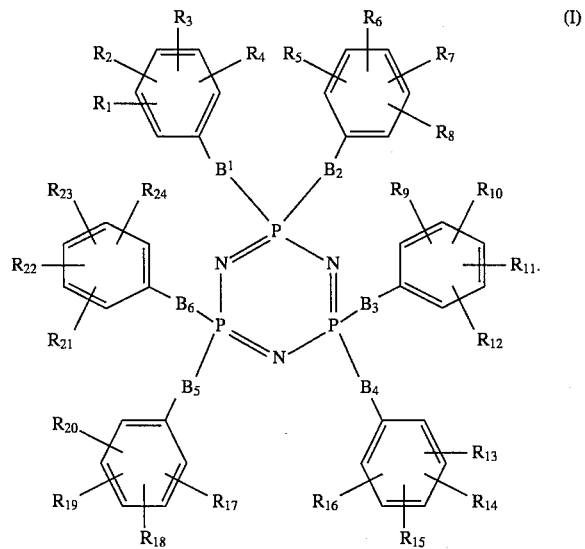

2 Claims, No Drawings

POSITIVE PHOTORESIST COMPOSITION CONTAINING NAPHTHOQUINONE DIAZIDE PHOSPHAZENE ESTERIFICATION PRODUCT

BACKGROUND OF THE INVENTION

1. Field of the invention

The present invention relates, in general, to novel photoresist compositions useful for fabrication processes for semiconductor devices and, more particularly, to novel photoresist compositions employing phosphazene compounds as ballast, unabsorbent of light at a band of i-line (wavelength 365 nm) and g-line (wavelength 436 nm) and superior in thermal resistance and sensitivity as well as resolution.

2. Description of the Prior Art

As high integration of semiconductor devices has been accelerated in the last few years, fine image-forming technologies useful for fabrication of semiconductor devices become highly precise. Correspondingly, photoresist used in the fine image-forming technologies is required to have a combination of high sensitivity, high resolution, and superior thermal resistance.

As a fine image-forming technology, there is extensively employed a lithography technology which takes advantage of a g-line with a wavelength of 436 nm and an i-line with a wavelength of 365 nm from a mercury lamp, a light source. In addition, there are various methods, what is called, next generation lithography technology, using an excimer laser (KrF, wavelength 248 nm), an X-ray and an electron beam.

Phenol novolak/naphthoquinone diazide-benzophenone resist compositions are widely used as photoresist for UV (g-line, i-line). In these resist compositions, benzophenone compounds serve as ballast and are exemplified by trihydroxy benzophenone (U.S. Pat. Nos. 3,666,473 and 4,115,128), tetrahydroxy benzophenone (Japanese Patent Laid-Open Publication Nos. Sho. 61-45240, Sho. 61-118744 and Sho. 62-280737) and so on. Herein, ballast means a kind of a latent compound which can function as a photosensitive agent through ether reaction of its photosensitive group, that is to say, a precursor compound having a photosensitive group.

However, since these exemplified compounds absorb light at a band of i-line which is most extensively used at present, the resulting photoresists are poor in transparency, which, in turn, deleteriously affect profile or resolution. In addition, the exemplified benzophenone compounds have low solubilities in resist solutions.

SUMMARY OF THE INVENTION

Accordingly, it is an object of the present invention to provide a photoresist composition, unabsorbent of light at a band of i-line and g-line.

It is another object of the present invention to provide a photoresist composition, superior in thermal resistance and in resolution.

It is a further object of the present invention to provide a photoresist composition having an improved solubility in resist solvent.

Based on the intensive research and study by the present inventors, the above objects could be accomplished by incorporating into a photoresist composition an appropriate form of a compound having phosphazene structure units, a compound having a framework of —$(P=N)_3$—, represented by the following formula I, which is unabsorbent of light at a band of i-line, in addition to being superior in thermal resistance and in solubility:

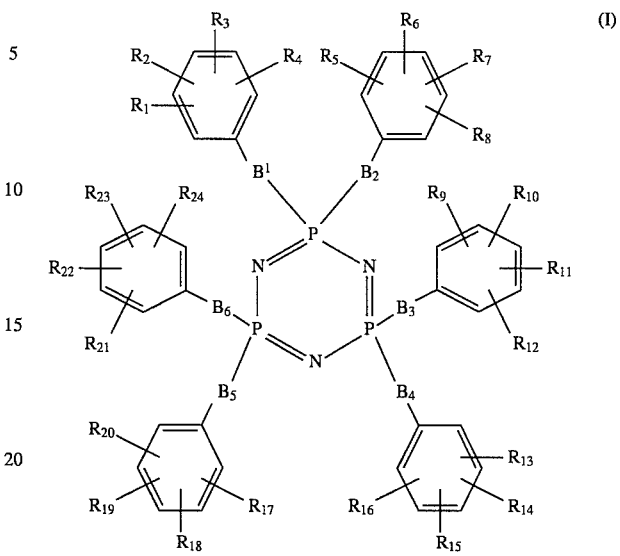

wherein $R_1$ through $R_{24}$ independently represent a hydrogen atom, a hydroxyl group, an alkoxy group or an alkyl group containing 1 to 4 carbon atoms and may be different from or the same with one another, at least one of which is the hydroxyl group. $B_1$ through $B_6$ are independently selected from a group consisting of oxygen, methyl oxygen and ethyl oxygen and may be different from or the same as one another.

In an aspect of the present invention, there is provided a positive photoresist composition, comprising an alkali soluble novolak resin, and an ester of quinone diazide compound and a a phosphazene type compound represented by formula I.

More preferably, the ester of the present invention is prepared by reacting 1,2-naphthoquinone-diazide-5- (or 4-) sulfonyl halide with a phosphazene type compound of formula I wherein the six radical groups, $R_1$ to $R_4$, $R_5$ to $R_8$, $R_9$ to $R_{12}$, $R_{13}$ to $R_{16}$, $R_{17}$ to $R_{20}$, and $R_{21}$ to $R_{24}$ (each being confined within one of the benzine rings), contain at least one hydroxyl group per benzene ring.

In accordance with a further aspect of the present invention, there is provided a photoresist composition, comprising at least one compound represented by formula I, at least one compound represented by formula II and an alkali soluble novolak resin.

These and other objects together with others not specifically mentioned will become clear to those skilled in the art as the following description proceeds.

DETAILED DESCRIPTION OF THE INVENTION

A phosphazene compound of formula I particularly suitable for the present invention is hexakis(hydroxyphenoxy) cyclotriphosphazene. For its preparation, hexachlorocyclotriphosphazene is reacted with methoxy phenol in the presence of base catalyst, to synthesize hexakis(methoxyphenoxy)cyclotriphosphazene which is then subjected to hydrolysis. In the synthesis, sodium, sodium hydride, sodium carbonate, pyridine or triethyl amine is used as the base catalyst, and preferred is sodium or sodium hydride. In the hydrolysis, N-methyl pyrrolidone, boron tribromide, boron trichloride, boron triiodide, iodotrimethyl silane or lithium diphenyl phosphite may be used, and of these compounds, boron tribromide, boron trichloride and boron triiodide are preferred.

In accordance with the present invention, hexakis (1,2-naphthoquinone-2-diazide-5-sulfonyloxy-phenoxy) cyclotriphosphazene is used as a photosensitive agent. For synthesis of the photosensitive agent useful in the present invention, hexakis(hydroxyphenoxy)cyclotriphosphazene is reacted with 1,2-naphthoquinone-2-diazide-5-sulfonyl halide in the presence of a base catalyst. Examples of base catalysts useful to synthesize the photosensitive agent of the present invention include pyridine, triethyl amine, sodiumhydroxy carbonate and sodium carbonate, and preferred are triethyl amine and pyridine.

Alkali soluble resins contained in the photoresist compositions of the present invention serve as film-forming materials. In the present invention, there is no particular limitation with regard to the alkali soluble resins. It is permitted to use alkali soluble novolak resins, typical film-forming materials used in conventional positive photoresist composition, which are generally prepared by condensing aromatic hydroxy compounds, such as phenol, cresol or xylenol, with formaldehydes, in the presence of acid catalyst.

As far as photoresist is concerned, it is prepared by dissolving hexakis(alkyl 1,2-naphthoquinone-2-diazide-5-sulfonyloxyphenoxy)cyclotriphosphazene, an ester compound of phosphazene and quinone diazide compound, and phenol novolak resin in an organic solvent. As the organic solvent, there is exemplified ethylene glycol, cyclohexanone, ethylene glycolmonoalkyl ether and acetates thereof, and ethyl lactate. Sole solvent is preferable, but a mixture of 2 species may, if necessary, be used.

The preferred embodiments of the present invention will now be further described with reference to specific examples.

EXAMPLE 1

10.00 g of hexachlorocyclotriphosphazene was dissolved in 150 ml of tetrahydrofuran and then, added with 11.50 g of oil-dispersed sodium hydride. To this solution, 200 ml of tetrahydrofuran containing 35.34 g of methoxy phenol was added dropwise, and the resulting solution was reacted at 66° C. for 24 hours, to synthesize hexakis(methoxyphenoxy) cyclotriphosphazene. This synthesized material was washed many times with methyl alcohol and further purified by twice precipitation in methyl alcohol and distilled water system. 68% yield.

The synthesized hexakis(methoxyphenoxy)cyclotriphosphazene was analyzed with a Fourier transform-infrared spectrometer (hereinafter referred to as "FT-IR"), a proton-nuclear magnetic resonance spectrometer (hereinafter referred to as "$^1$H-NMR"), and a phosphorous-nuclear magnetic resonance spectrometer (hereinafter referred to as "$^{31}$P-NMR"), to confirm its synthesis state.

2.18 g of the hexakis (methoxyphenoxy) cyclotriphosphazene synthesized was dissolved in 50 ml of dichloromethane, and to this solution was added dropwise 1.74 ml of boron tribromide, to prepare hexakis (hydroxyphenoxy) cyclotriphosphazene. Purification was carried out by washing the prepared material several times with distilled water. 82.58% yield.

Analysis for the hexakis(hydroxyphenoxy) cyclotriphosphazene prepared was executed with FT-IR, $^1$H-NMR and $^{31}$P-NMR.

EXAMPLE 2

The hexakis(methoxyphenoxy)cyclotriphosphazene was synthesized in a similar manner to that of Example 1, except that triethyl amine was used in place of oil-dispersed sodium hydride. 58.40% yield.

FT-IR, $^1$H-NMR and $^{31}$P-NMR were used for analysis of the hexakis(methoxyphenoxy)cyclotriphosphazene synthesized.

6.54 g of the hexakis(methoxyphenoxy)cyclotriphosphazene synthesized was dissolved in 150 ml of dichloromethane, and to this solution was added dropwise a mixture of 3.22 ml of boron tribromide and 50 ml of dichloromethane, to prepare hexakis(hydroxyphenoxy)cyclotriphosphazene which was then washed several times with distilled water. 83.50% yield.

Analysis for the hexakis(hydroxyphenoxy)cyclotri phosphazene prepared was carried out with FT-IR, $^1$H-NMR and $^{31}$P-NMR.

EXAMPLE 3

The hexakis(hydroxyphenoxy)cyclotriphosphazene prepared in Examples 1 and 2 was reacted with 1,2-naphthoquinone-2-diazide-5-sulfonyl chloride in such a way that the mole ratios of the former to the latter were 1:6, 1:5, 1:4, 1:3.5, and 1:3, in the presence of triethyl amine, a catalyst. Hexakis[(1,2-naphthoquinone-2-diazide-5-sulfonyloxy)phenoxy]cyclotriphosphazene thus synthesized at each mole ratio was purified by washing with methyl alcohol, in combination with distilled water and alone.

EXAMPLE 4

Synthesis of hexakis (dimethoxyphenoxy) cyclotriphosphazene was accomplished in a similar manner to that of Example 1, except that dimethoxy phenol and metal sodium were used in place of methoxy phenol and oil-dispersed sodium hydride, respectively and the mole ratios of hexachloro cyclotriphosphazene to dimethoxy phenol were 1:4, 1:6, 1:9 and 1:10.

The synthesized hexakis(dimethoxyphenoxy)cyclo triphosphazene was analyzed with FT-IR, 1H-NMR, a carbon-nuclear magnetic resonance spectrometer (hereinafter referred to as "$^{13}$C-NMR") and $^{31}$P-NMR.

After dissolving the hexakis(dimethoxyphenoxy)cyclo triphosphazene in methane, boron tribromide was added dropwise into the solution, to prepare hexakis(dihydroxyphenoxy)cyclotriphosphazene which was then washed with distilled water.

Analysis for the hexakis(dihydroxyphenoxy) cyclotriphosphazene prepared carried out with FT-IR, $^1$H-NMR, $^{13}$C-NMR and $^{31}$P-NMR.

EXAMPLE 5

The hexakis(dihydroxyphenoxy)cyclotriphosphazene prepared in Example 4 was reacted with 1,2-naphthoquinone-2-diazide-5 -sulfonyl chloride in such a manner that the mole ratios of the former to the latter were 1:6, 1:9, 1:10, and 1:12, in the presence of triethyl amine, a catalyst. Hexakis[(di-1,2 -naphthoquinone-2-diazide-5-sulfonyloxy)phenoxy]cyclotriphosphazene thus synthesized at each mole ratio was purified by reprecipitaion in a mixture of methyl alcohol and distilled water and in sole methyl alcohol.

EXAMPLE 6

10.00 g of hexachlorocyclotriphosphazene was dissolved in 150 ml of tetrahydrofuran and then, added with 11.50 g of oil-dispersed sodium hydride. To this solution, 200 ml of tetrahydrofuran containing 47.58 g of trimethoxy phenol was added dropwise, and the resulting solution proceeded into reaction at 66° C. for 24 hours, to synthesize hexakis(trimethoxyphenoxy)cyclotriphosphazene. This synthesized material was washed many times with methyl alcohol and further purified by twice precipitation in methyl alcohol and distilled water system. 64.50% yield.

The synthesized hexakis(trimethoxyphenoxy) cyclotriphosphazene was analyzed with FT-IR, $^1$H-NMR, $^{13}$C-NMR and $^{31}$P-NMR.

The hexakis(trimethoxyphenoxy) cyclotriphosphazene synthesized was dissolved in dichloromethane, and to this solution was added slowly dropwise boron tribromide with care, to prepare hexakis(trihydroxyphenoxy) cyclotriphosphazene and mixture thereof. Purification was carried out by washing the prepared materials several times with distilled water. 82.58% yield.

Analysis for the hexakis(trihydroxyphenoxy) cyclotriphosphazene prepared was executed with FT-IR, $^1$H-NMR and $^{31}$P-NMR.

EXAMPLE 7

The hexakis(trihydroxyphenoxy) cyclotriphosphazene prepared in Example 6 was reacted with 1,2-naphthoquinone-2-diazide-5-sulfonyl chloride in such a manner that the mole ratios of the former to the latter were 1:6, 1:10, 1:12, 1:15 and 1:18, in the presence of triethyl amine, a catalyst. Hexakis[(tri-1,2-naphthoquinone-2-diazide-5-sulfonyloxy)phenoxy]cyclotriphosphazene thus synthesized at each mole ratio was purified by reprecipitaion in a mixture of methyl alcohol and distilled water and in sole methyl alcohol.

EXAMPLE 8

In the presence of triethyl amine, a catalyst, hexachlorocyclotriphosphazene was reacted with 2-methoxy-4-methyl phenol, to synthesize hexakis(2-methoxy-4-methylphenoxy)cyclo triphosphazene which was analyzed with FT-IR, $^1$H-NMR, $^{13}$C-NMR and $^{31}$P-NMR.

10.00 g of hexakis(2-methoxy-4-methylphenoxy)cyclotriphophagen synthesized was dissolved in 250 ml of dichloromethane, and then. to this solution was added dropwise 6.02 g of boron tribromide, to prepare hexakis(2-hydroxy-4-methylphenoxy)cyclotriphosphazene. This prepared material was washed 3 to 5 times with distilled water.

The prepared hexakis(2-hydroxy-4-methylphenoxy)cyclo triphosphazene was analyzed with FT-IR, $^1$H-NMR, $^{13}$C-NMR and $^{31}$P-NMR.

EXAMPLE 9

The hexakis(2-hydroxy-4-methylphenoxy)cyclotriphosphazene prepared in Example 8 was reacted with 1,2-naphthoquinone-2-diazide-5-sulfonyl chloride in such a manner that the mole ratio of the former to the latter was 1:6, in the presence of triethyl amine, a catalyst. Hexakis[2-(1,2-naphthoquinone-2-diazide-5-sulfonyloxy)-4-methylphenoxy]cyclotriphosphazene thus synthesized was purified by washing with methyl alcohol several times.

EXAMPLE 10

10 g of phenolic novolak resin, 2.7 g of hexakis[(1,2-naphthoquinone-2-diazide-5-sulfonyloxy)phenoxy]cyclotriphosphazene prepared in Example 3, a dissolution-retardant, were dissolved in 33.5 g of ethylene glycolmonoether acetate solvent and filtered by a filter of 0.2 μm, to prepare resist. The filtered solution was coated on a silicon wafer in a thickness of 1 μm by a spin-coater and then, preheated at a temperature of 100° to 110° C. for 1 minute. After being exposed to i-line (wavelength 365 nm) at a dose of 150 to 250 mJ/cm$^2$, the silicon wafer coated was subjected to thermal treatment at a temperature of 100° to 120° C. for a period of 40 to 60 seconds. Development in 2.38 wt % tetraammonium hydroxide yielded a positive pattern superior in resolution.

EXAMPLE 11

10 g of phenolic novolak resin, 2.5 g of hexakis[(di-1,2-naphthoquinone-2-diazide-5-sulfonyloxy)phenoxy]cyclotriphosphazene prepared in Example 5, a dissolution-retardant, were dissolved in 32.3 g of ethylene glycolmonoether acetate solvent and filtered, to prepare resist. The filtered solution was coated on a silicon wafer in a thickness of 1 μm by a spin-coater and then, preheated at 100° C. for 1 minute. After being exposed to i-line at a dose of 150 to 250 mJ/cm$^2$, the silicon wafer coated was subjected to thermal treatment at 100° C. for a period of 40 to 60 seconds. Development in 2.38 wt % tetraammonium hydroxide yielded a positive pattern superior in resolution.

EXAMPLE 12

5 g of phenolic novolak resin, 1.3 g of hexakis[(tri-1,2-naphthoquinone-2-diazide-5-sulfonyloxy)phenoxy]cyclotriphosphazene prepared in Example 7, a dissolution-retardant, were dissolved in 16.0 g of ethylene glycolmonoether acetate solvent, to prepare resist. The resulting solution was coated on a silicon wafer in a thickness of 1 μm by a spin-coater and then, preheated at 100° C. for 1 minute. After being exposed to i-line at a dose of 150 to 250 mJ/cm$^2$, the silicon wafer coated was subjected to thermal treatment at 100° C. for 60 seconds. Development in 2.38 wt % tetraammonium hydroxide yielded a positive pattern superior in resolution.

EXAMPLE 13

10 g of phenolic novolak resin, 2.00 g of hexakis[(1,2-naphthoquinone-2-diazide-5-sulfonyloxy)phenoxy]cyclotriphosphazene prepared in Example 3, and 0.5 g of hexakis(4-methoxyphenoxy) cyclotriphosphazene which would act as a low molecular weight additive to increase the solubility were dissolved in 16.25 g of ethylene glycolmonoether acetate solvent, to prepare resist. The resulting solution was coated on a silicon wafer in a thickness of 1 μm by a spin-coater and then, preheated at 100° C. for 1 minute. After being exposed to i-line (wavelength 365 nm) at a dose of 150 to 250 mJ/cm$^2$, the silicon wafer coated was subjected to thermal treatment at a temperature of 100° to 120° C. for 60 seconds. Development in 2.38 wt % tetraammonium hydroxide for 90 seconds yielded a positive pattern superior in resolution.

The ballasts to the present invention were tested for sensitivity and thermal resistance and the results are shown as given in the following Tables 1 and 2, along with the physical properties of conventional photoresist compositions.

TABLE 1

Comparison of High Sensitivity

| Material | ε (1/mol · cm) Sensitivity |
|---|---|
| Phosphazene Cpd. (Formula II) | 51,000–70,000 |
| tri-HBP + NAC-5 | 24,000–26,000 |
| tetra-HBP + NAC-5 | 32,000–36,000 |

[Footnote] NAC-5:1,2-naphthoquinone-2-diazide-5-sulfonyl halide tri-HBP: trihydroxy benzophenone tetra-HBP: tetrahydroxy benzophenone

TABLE 2

Comparison of Thermal Resistance

| Material | °C. Melting Point |
|---|---|
| Phosphazene Cpd. (Formula I) | 240–260 |
| tri-HBP | 137–144 |
| tetra-HBP | 200–218 |

As apparent from the tables, the photoresist composition according to the present invention exhibits excellent effects in sensitivity and thermal resistance relative to conventional ones. For example, in melting point, the ballast of the present invention is higher by from 22° even to 123° C. than conventional one. This high melting point presents good thermal resistance to the resulting resist, so that the resist is rarely decomposed upon baking, which prevents distortion of pattern.

As to dissolution property in resist solvent, photosensitive agents from conventional ballast, for example, tetrahydroxy benzophenone wherein all photosensitive groups are substituted have a solubility of about 20%, while those from present ballast, e.g. phosphazene compounds in which all photosensitive groups are substituted, have a solubility of about 100%.

In addition, it is proved that the ballast according to the present invention is superior to conventional ones in resolution and dissolution retardancy.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. A positive photoresist composition, comprising an alkali soluble novolak resin and an ester of 1,2-naphthoquinone-2-diazide-5-(or 4-)sulfonyl halide with a phosphazene compound in accordance with formula I:

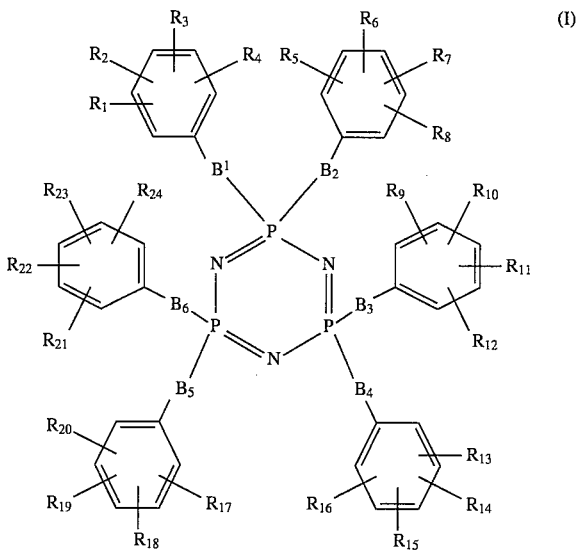

wherein $R_1$ through $R_{24}$ are different from or the same as one another, $R_1$ through $R_{24}$ being independently selected from the group consisting of a hydrogen atom, a hydroxyl group, an alkoxy group, and an alkyl group containing 1 to 4 carbon atoms, at least one of $R_1$ through $R_{24}$ being of the hydroxyl group; and wherein $B_1$ through $B_6$ are different from or the same as one another, $B_1$ through $B_6$ being independently selected from the group consisting of oxygen, methyl oxygen and ethyl oxygen.

2. The positive photoresist composition in accordance with claim 1, wherein $R_1$ to $R_4$, $R_5$ to $R_8$, $R_9$ to $R_{12}$, $R_{13}$ to R16, $R_{17}$ to $R_{20}$, and $R_{21}$ to $R_{24}$ define separate radical groups, each of said radical groups being confined within separate benzene rings of the formula I, each of the benezene rings containing at least one hydroxyl group.

* * * * *